United States Patent
Förster

(10) Patent No.: US 6,309,213 B1
(45) Date of Patent: Oct. 30, 2001

(54) EXPANSION APPLIANCE FOR CORRECTING TOOTH MISALIGNMENTS

(75) Inventor: Rolf Förster, Pforzheim (DE)

(73) Assignee: Bernhard Forster, Pforzheim (DE)

( * ) Notice: Subject to any disclaimer, the term of this patent is extended or adjusted under 35 U.S.C. 154(b) by 0 days.

(21) Appl. No.: 09/466,461

(22) Filed: Dec. 17, 1999

(30) Foreign Application Priority Data

Dec. 17, 1998 (DE) .............................. 198 58 434
Apr. 28, 1999 (DE) .............................. 199 19 329

(51) Int. Cl.[7] .................................................. A61C 3/00
(52) U.S. Cl. ...................................................... 433/7
(58) Field of Search ...................................... 433/7

(56) References Cited

U.S. PATENT DOCUMENTS 3,284,902 * 11/1966 Dillberg et al. ......................... 433/7
5,167,500   12/1992 Miura ....................................... 433/7

FOREIGN PATENT DOCUMENTS

283235 * 9/1952 (CH) ......................................... 433/7
0817596   1/1998 (EP) .
998076 * 1/1952 (FR) ......................................... 433/7
608117 * 9/1960 (IT) ......................................... 433/7

* cited by examiner

Primary Examiner—John J. Wilson
(74) Attorney, Agent, or Firm—Horst M. Kasper

(57) ABSTRACT

Expansion appliance for correcting tooth misalignments having the following features: a first member (1), a second member (2), a spindle (3) which, for changing the distance between the first (1) and the second member (2), engages the two members (1, 2) in such a way that the distance can be varied by a predeterminable limited magnitude in the longitudinal direction of the spindle (3) in the stationary condition of the latter. There are provided two parallel guide rods (21), located on both sides of the spindle (3). For guiding the member (1, 2) in straight alignment the guide rods (21) are received and guided in holes (20) in the two members (1, 2) which extend in parallel one to the other and each of which is open toward the respective other member (2, 1). A compression spring (2) is tensioned between at least one end of each guide rod (21) and the respective opposite end of the hole (20), this end of the hole (20) being closed.

25 Claims, 7 Drawing Sheets

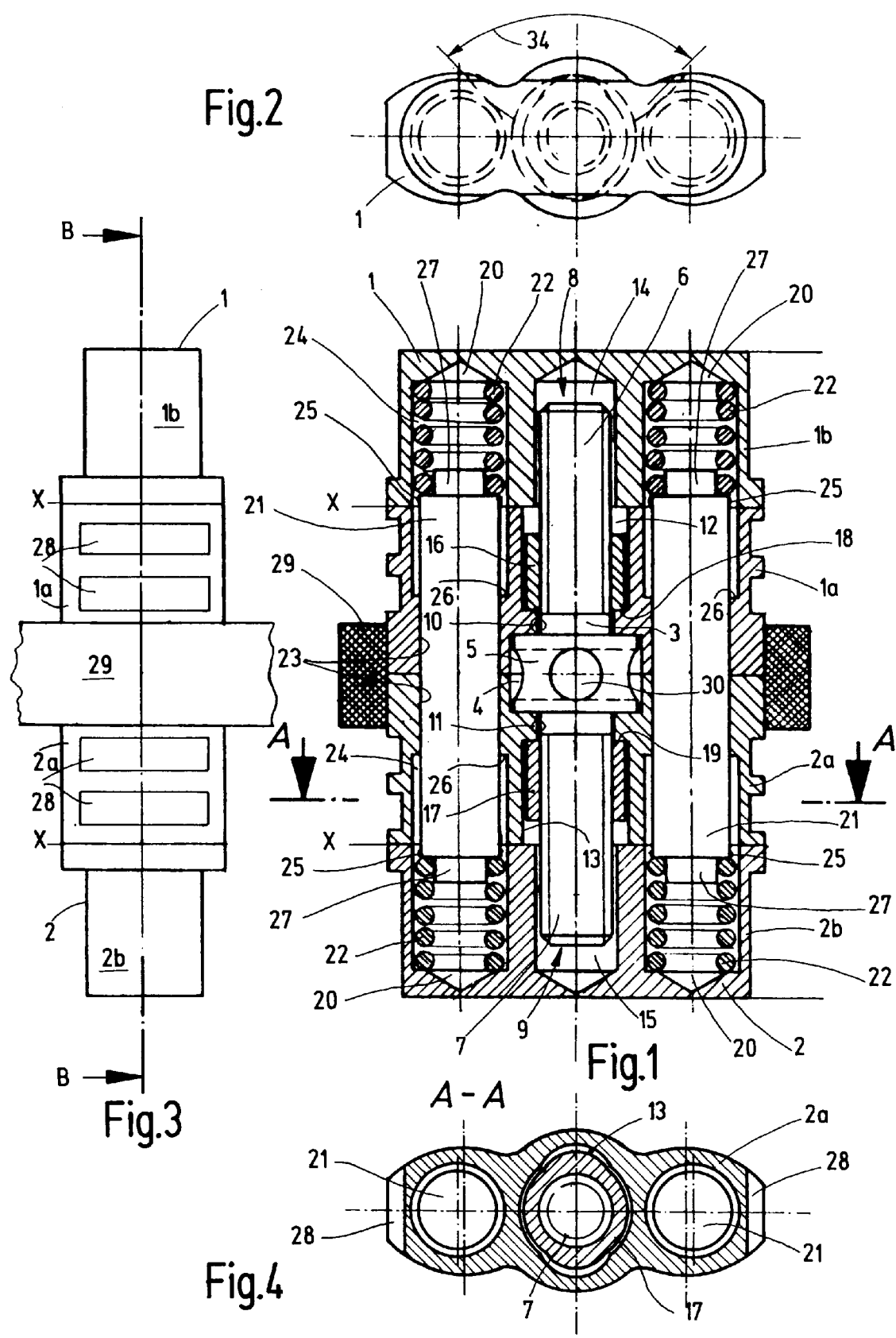

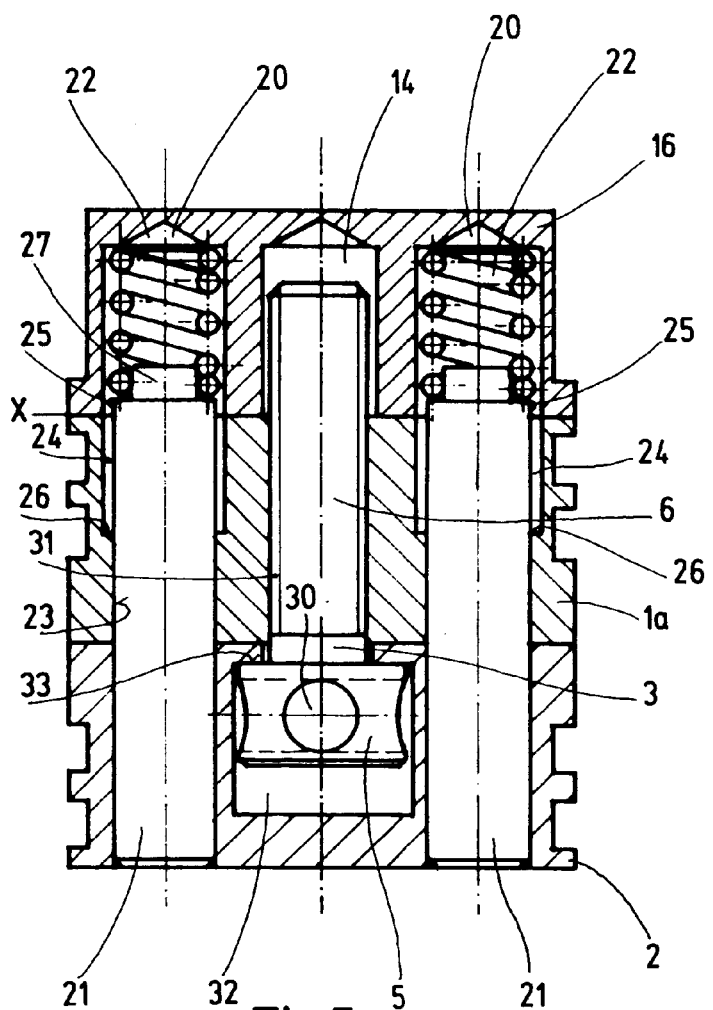
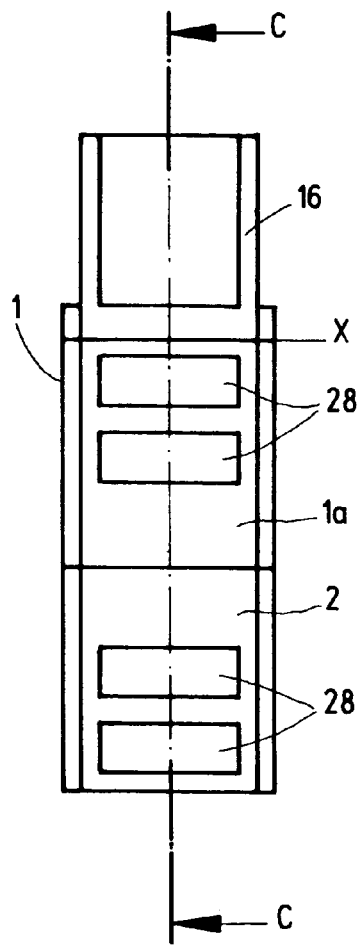
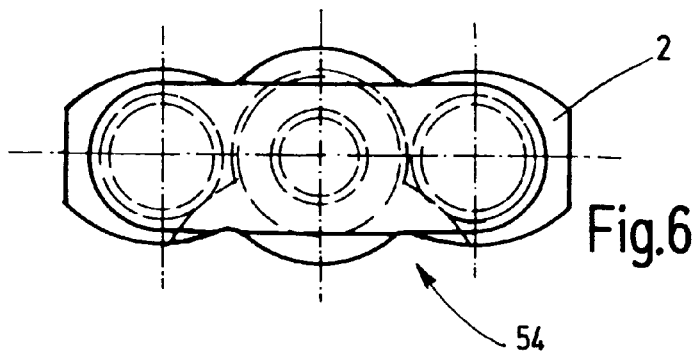
Fig.5
Fig.6
Fig.7

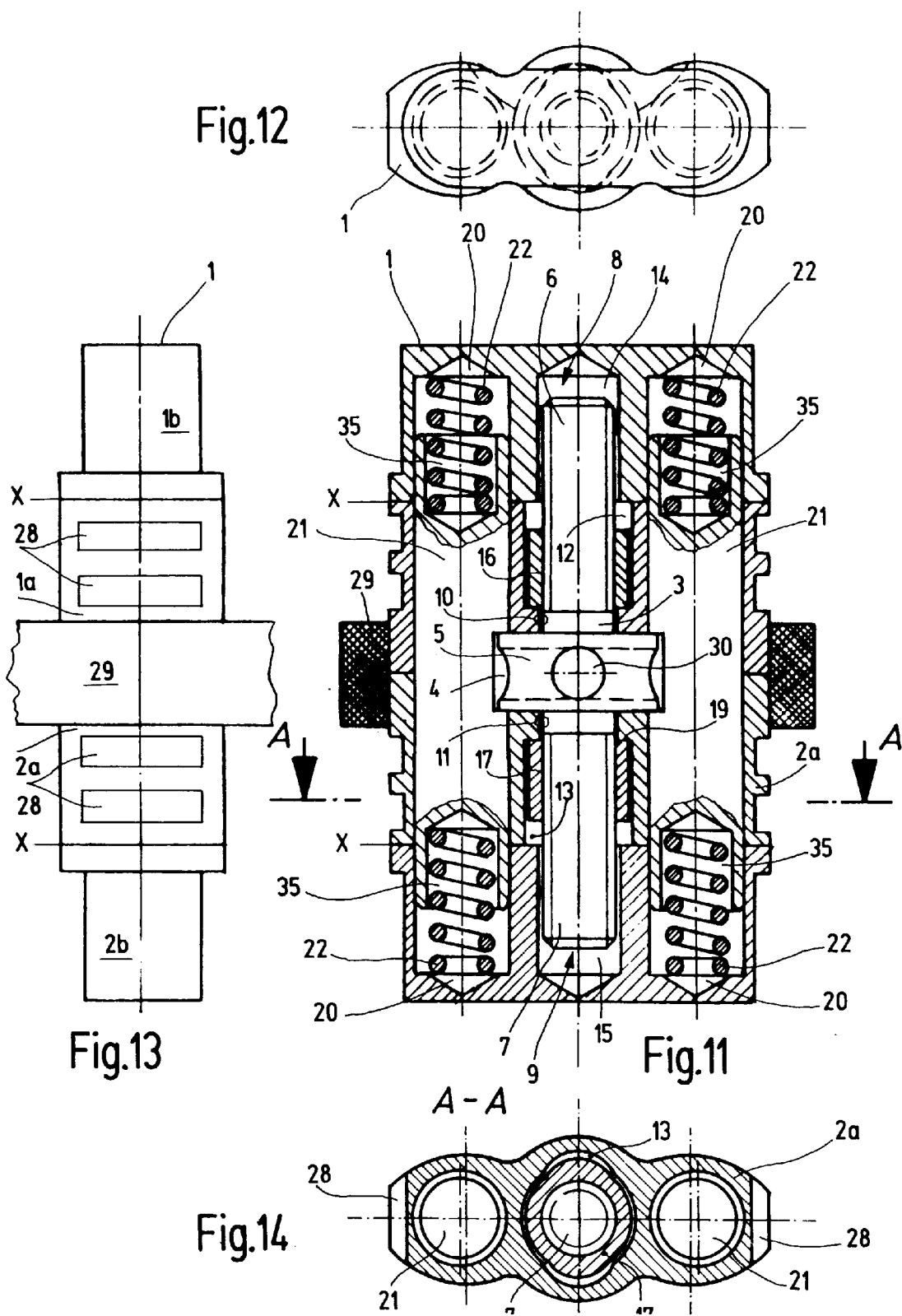

A-A

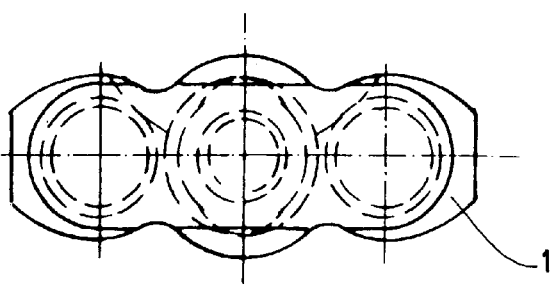
Fig.20
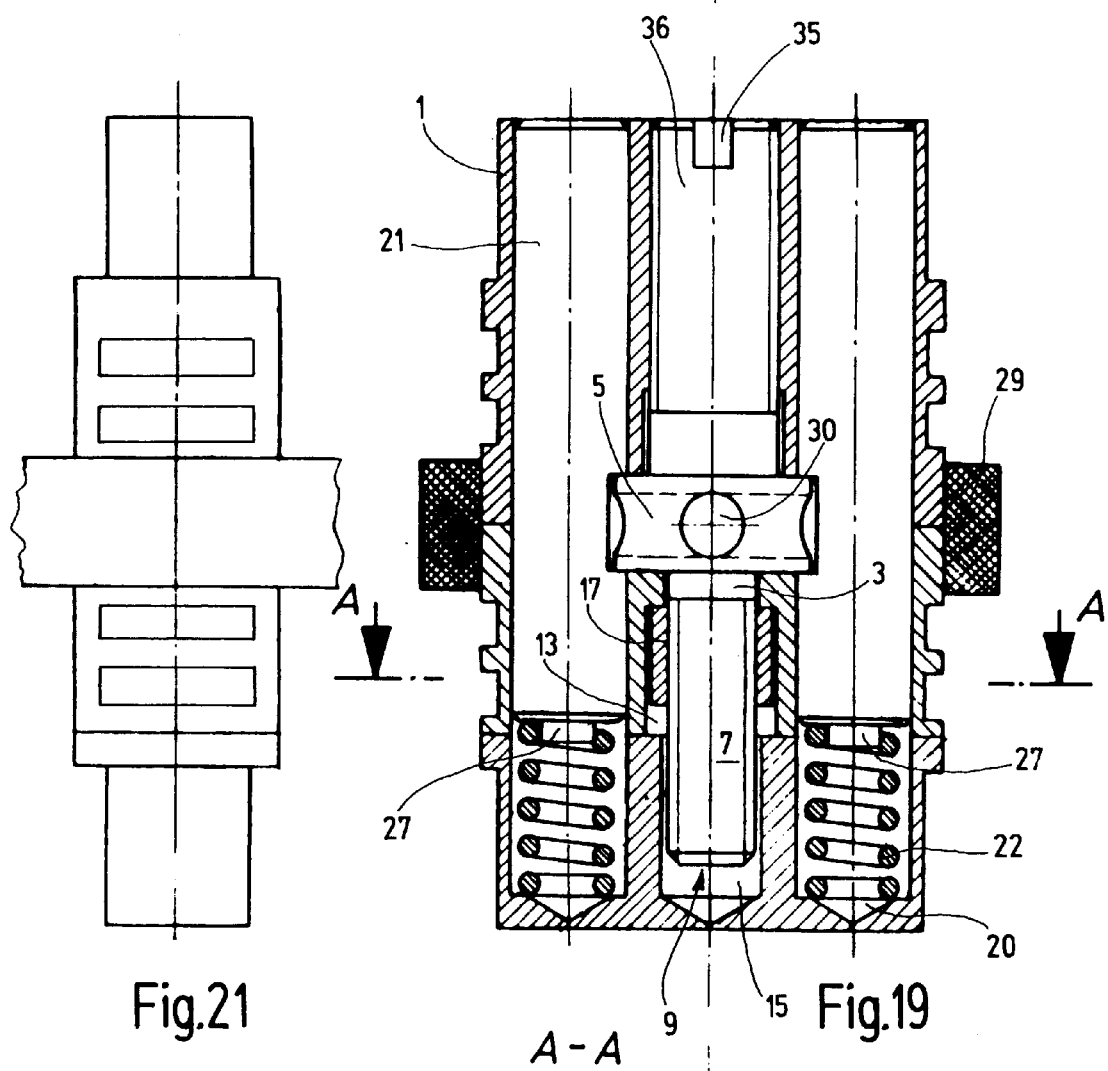
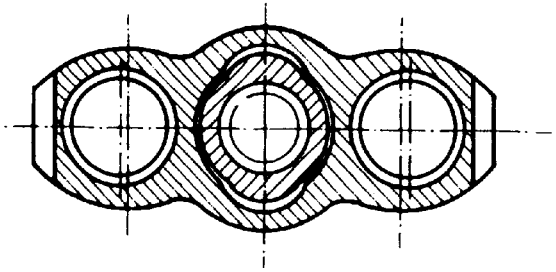
Fig.21　　Fig.19
A-A
Fig.22

EXPANSION APPLIANCE FOR CORRECTING TOOTH MISALIGNMENTS

SPECIFICATION

The present invention is based on an expansion appliance having the features indicated in the preamble of Claim 1. An expansion appliance of this kind is known from WO96/28110. The known expansion appliance comprises two members the relative distance of which can be varied by means of a double spindle by means of which the two members, being guided in straight alignment by two parallel guide rods, can be driven away one from the other. The spindle does not act directly on the members but rather indirectly via compression springs. The springs are coiled springs that are tensioned as the spindle is rotated and that determine the expansion force. To this end, each of the two members accommodates a lengthwise displaceable, but non-rotatable nut which is engaged by one of the two threaded sections of the spindle that extend from an actuating section. The nut exhibits a flange. The spring is supported on that flange by one of its ends and on the end of an orifice in the respective member by its other end. By rotating the spindle, the nuts can be moved away from the actuating section of the spindle so that the springs are tensioned. The inherent tension force of the springs can then produce a change in tooth position in a patient's mouth, which comes to its end when the two members of the expansion appliance come to rest against the flanges of the two nuts. If the tooth position is then to be changed further, the two springs must be re-tensioned by rotation of the spindle.

The maximally possible expansion of the appliance is determined by the length of the threaded sections of the double spindle, while the expansion force is determined by the springs. This distinguishes such an expansion appliance from a non-resilient jackscrew of the kind disclosed by U.S. Pat. No. 5,167,500 as prior art, where the two variable-distance members are displaced directly by means of a double spindle having sections of oppositely directed threads, not by means of a spring in order to achieve high correction forces, such a jackscrew can always be expanded by no more than 0.25 mm. For a typical tooth correction with 4 mm of tooth movement, the patient must therefore visit the doctor 16 times in order to have the jackscrew readjusted, which is laborious and tiresome.

An advantage of the expansion appliance using a spring, as disclosed by WO96/28110, over the springlass jackscrew lies in the fact that due to its compressibility, it can be removed from and reinstalled in the dentition more easily, and not only by the doctor but also by the patient himself/herself. Although the springs of the expansion appliance known from WO/96/28110 are encapsulated in a recess in the two members, and the point of access to the recess is sealed by an O ring surrounding the spindle shaft, liquid food particles may still penetrate into the area of the springs, presumably due to a pumping effect which may occur not only during removal and reinstallation of the expansion appliance in the dentition but also when speaking and, especially, when chewing. The trapped food particles may then form hard depositions (tartar) which may cause the springs to become jammed, obstructed and blocked.

The present invention now has for its object to provide an expansion appliance which reduces the risk of food particles obstructing the expansion of the springs. The constructional measures necessary for this purpose, however, must not have the result to make the expansion appliance thicker than that known from WO96/28110, the space available in the mouth being small. The larger a foreign body, which is to be introduced into the mouth, the more will speaking be hindered, and the torque is so sensitive that it senses changes already in the range of a tenth of a millimeter. Consequently, the thickness of the expansion appliance may not be increased by protective measures for the springs.

This object is achieved by an expansion appliance having the features specified in Claim 1.

In the case of an expansion appliance using a double spindle, this object is further achieved by the features indicated in Claim 19. The dependent Claims 20 and 21 further provide, as means for achieving the object, an expansion appliance with a spindle that exhibits only one threaded section instead of two threaded sections.

In an expansion appliance according to the invention, contrary to that disclosed by WO96/28110, the springs do not enclose a threaded section of the spindle or a nut screwed onto the spindle, but have been shifted toward the guide rods. But contrary to the elastic expansion appliance disclosed by U.S. Pat. No. 5,167,500-A the springs are not arranged on a guide rod between the two members of the ole in the respective member of the expansion appliance, the end of that hole being closed. Each spring is, therefore, located in a chamber that is closed on the one hand by the walls of the respective member of the expansion appliance and, on the other hand, by the guide rod that is guided in the hole. This provides significant advantages:

- The entire length over which the respective guide rod is guided in the member is available for sealing the space in which the respective spring is enclosed.
- The gap between the guide rod and the wall in each section of the holes, in which the guide rod is guided, may be considerably narrower than the gap between the spindle and the edge of the opening giving access to the orifice in the member, and also much smaller than the gap between the nut and the wall of the orifice surrounding the latter.
- A pumping effect, that may suck liquid food particles into the area of the springs, cannot occur.
- The springs are tensioned only at the beginning of correction of the tooth position, when the expansion appliance is still absolutely clean. Thereafter, the spindle only serves to control relaxation of the springs. During the relaxation process, any depositions will, however, have a much less restricting effect that in the prior art, during re-tensioning of the springs.
- If any liquid food particles should still penetrate into the gap between the guide rods and the wall of the respective hole in which they are guided, then they will be transported to the outside by the progressive expansion of the springs.
- By having the springs shifted to the ends of the guide rods, no spring surrounding the spindle is needed. The expansion appliance according to the invention can, therefore, be made less thick than an expansion appliance according to WE96/28110. This is so because the springs provided at the ends of the guide rods may be made thinner without any problem. The resulting loss in spring force of the individual spring is more than compensated by the fact that springs, acting in parallel, are provided on both guide rods.
- Contrary to a system with centrally arranged springs, the arrangement of springs on both guide rods prevents any tilting moments from occurring and provides well-balanced distribution of forces.

Seals are no longer required.

The guide rods and the sections of the holes in which the are guided exhibit, preferably, a cylindrical shape; this makes it possible to make the annular gaps between the guide rods and the sections of the holes, in which they are guided, especially narrow.

If the guide rods are guided over their full length at the beginning of the expansion process, then they develop the greatest sealing effect. Given the fact, however, that the length over which the guide rods are guided must not drop below a minimum value at the end of the expansion range if parallel guiding of the members is to be guaranteed, it has been found that the sealing effect is sufficiently good even in this state. This makes it possible to limit the length, over which the guide rods are guided, from the beginning and to design the holes in which the guide rods are arranged in such a way as to provide, between the sections guiding the guide rods and the end of each guide rod, a section whose interior width is larger than the interior width of the guiding section. This provides the advantage that a thicker portion, an enlargement or a radial projection formed in some other way may be provided at the end of the guide rod, which cannot pass through the section of the hole that serves to guide the guide rod, being stopped by the transition between the wider and the narrower sections of the hole, whereby the maximally possible expansion of the expansion appliance is determined. It is especially easy in this connection to notch the ends of the guide rods for displacing some of the material radially to the outside. This is sufficient to ensure that the guide rods will be prevented from sliding out of the holes, and from falling to pieces, under the pressure of the pre-stressed springs, once the expansion appliance has been assembled.

To provide an enlarged section in the holes, following the section guiding the guide rods, provides the additional advantage that any liquid, that may enter the arrangement in the most unfavorable of all cases, any initially gather in the annular space between the guide rod and the enlarged section of the hole, before advancing to the spring. In addition, this arrangement provides the possibility to make the diameter of the spring a little larger and, thus, the spring a little stronger.

The coiled springs are arranged in the bores of the members, in which the guide rods are accommodated as well, between their ends and the ends of the bores and are tensioned by compression. They may rest against the plain ends of the guide rods. Preferably, the guide rods carry on their respective ends a thinner lengthwise extension that has a certain length engaged in the adjacent coiled spring, whereby the latter is centered. According to another advantageous further development, the guide rods are provided on their ends with a lengthwise extending blind hole in which part of the length of the adjacent coiled spring is accommodated. Compared with the embodiment described before this design provides the advantage that it permits the use of guide rods of greater length, without any need to shorten the springs and without being forced to increase the size of the entire expansion appliance. Longer guide rods provide, however, improved guidance and increase the expansion range of the expansion appliance.

In order to permit the expansion appliance to be assembled, in spite of the radial projections of the guide rods, it would be imaginable to design the holes in the members as through-holes and to close the outer ends of the holes subsequently by welding on or pressing in small plates or other end pieces. Preferably, however, the members are given a two-part design, i.e. divided crosswise to the longitudinal direction of the guide rods, with the joint face intersecting the enlarged sections of the holes. Conveniently, the joint face is a plane. Due to the division it is then possible to first fit the guide rods, which initially do not exhibit a radial projection, in the elements of the member with their narrow guide bores, to thereafter produce the radial projections by notching or upsetting, to insert the springs into the enlarged bores of the outer elements of the members, to joint the latter to the other elements of the members and to firmly connected them with the latter by hard soldering or welding, especially by laser welding.

The spindle must be mounted in the expansion appliance in such a way that the two members of the expansion appliance, which are variable with respect to their relative spacing, are captively held together. According to the prior art as disclosed by EP 0 817 596 this is achieved by providing stops between the two nuts mounted on the double spindle and the actuating section of the spindle in the two members, which stops act to limit the maximum spacing which the two members can assume. The expansion appliance according to the present invention also makes convenient use of stops acting between the spindle and the two members of the expansion appliance for captively holding together the spindle and the two members of the expansion appliance.

Claims 2 and 3 propose an especially suitable constructional design for an expansion appliance using a double spindle. With respect to expansion appliances using a single spindle, Claims 4 and 5 provide a suitable constructional design. These embodiments distinguish themselves by an especially compact design and their protected arrangement of the spindle, and they can be produced easily and at low cost. In this connection, the before-mentioned division of the members offers yet another advantage: It facilitates the process of mounting the nuts for the spindle. Since a stop is provided in the respective member between the nut and the actuating section of the spindle, the nut cannot be fitted in the respective orifice of the member from the side of the actuating section of the spindle; rather, the orifice must be accessible from the opposite end. Easy access is permitted by giving the members a two-part design. The nuts can now be inserted into the orifice of the respective member from the outer end of the orifice. The orifices are closed when both elements of the respective member are firmly joined one to the other.

Generally, it will be sufficient to provide a spring only on one end of the guide rods. Preferably, however, a spring is provided on each of the two ends of each guide rod. This increases the expansion range of the expansion appliance without increasing the expansion force. Preferably, the springs are of identical design.

Suitable as compression springs are, especially, springs made from a shape-memory allow which is pseudoelastic at the temperatures prevailing in the mouth.

Preferred shape-memory alloys are alloys based on nickel and titanium, which contain nickel and titanium in approximately equal atomic percentages. Alloys of this kind can exist, depending on the temperature selected, in either the austenitic or martensitic state. Martensite is present at lower temperatures, austenite at higher temperatures. The temperature at which the alloy begins to convert from austenite to martensite during cooling is called the Ms point. In the martensitic state below the Ms point, alloys of this kind can exhibit shape memory: a plastic deformation that has occurred in the martensitic state can be reversed by heating to a temperature above the Ms point. In a temperature range just above the Ms point, a shape-memory alloy of this kind can exhibit pseudoelastic behavior. This pseudoelastic behavior is characterized by the fact that the force required for increasing elongation of the material initially rises sharply as in the case of an austenite, but then, after reaching an elongation of approximately 1% to 2%, increases only slightly as elongation progresses further, and does not increase steeply again until reaching greater elongations of 6% to 8%. The intermediate elongation region is called the "martensite plateau," the name deriving from the fact that martensite forms in the alloy in response to the tensile stress. When the tension on the material is released, it reverts to the austenitic state. These pseudoelastic elongations are highly reversible up to elongations of more than 6% to 8%. Because of the pronounced martensite plateau, pseudoelasticity does not obey Hooke's law. Springs which exhibit this kind of pseudoelastic behavior are thus particularly suitable for the purposes of the present invention, since for spring travels in the region of the martensite plateau, the return force of the spring is almost independent of spring travel. An expansion appliance according to the invention using a pseudoelastic spring has the advantage that the spring tension will practically not drop for the duration of the treatment. This is favorable for achieving rapid correction of the tooth position.

Preferably, the expansion appliance according to Claims 2, 3 and 19 has a symmetrical design with equal guide rods, equal springs, equal members and equal nuts, which is an advantage in terms of low-cost production.

If a small expansion range is sufficient for correcting the tooth position, a simplified expansion appliance, compared with the embodiment according to Claims 3 and 19, may be used which is the object of Claims 4 and 20. Instead of having a double spindle, this expansion appliance uses a spindle with only one threaded section projecting from the actuating section. A spindle of that kind is called "head spindle" hereafter. In the case of Claims 4 and 20, the actuating section, or head of the head spindle, is located displaceably in an orifice of the second member, whereas the threaded section is threaded into a threaded bore in the first member. A comparable effect can be achieved in an embodiment having the features of Claims 5 and 21, where the head of the spindle is located, essentially fixed against displacement, in an orifice in the second member, whereas a nut, into which the threaded section of the spindle is threaded, is arranged in an orifice in the member in non-rotatable but longitudinally displaceable fashion.

Springs may be provided on both ends of the guide rods. Instead of such a "floating" support of the guide rods it is preferred, in the case of the expansion appliances according to Claims 4, 5, 20 and 21, to fix the guide rods in the second member, in which the head of the spindle is arranged, and to provide the springs only on the opposite ends of the guide rods in the first member, in the same manner as in an expansion appliance according to Claims 3 and 9.

A further embodiment of the invention distinguishes itself by the fact that although it comprises a double spindle, only one of its threaded sections carries a nut arranged in an orifice, in the one member of the expansion appliance, for limited displacement between stops. The other threaded section is threaded into a threaded bore provided directly in the other member of the expansion appliance. Rotation of the spindle has in this case the effect that on the one hand the two members of the expansion appliance are moved apart a certain distance and that on the other hand part of the expansion range of the springs is released. This permits that threaded section of the spindle, which is directly screwed into the one member, to be made thicker than the other threaded section. The end of the thicker threaded section can then be provided with a diagonal slot for a screwdriver blade for adjusting the spindle, which is easier than turning the actuating section of the spindle by quarter circles. If a diagonal slot were provided in a thinner threaded section (after deduction of the turns the threaded section typically has a diameter of only 1 mm), then there would be a considerable risk for the slot to break apart under the pressure of a screwdriver blade. Further advantages of this embodiment lie in the fact that it uses one nut less and that it facilitates the assembly process, the latter also because it is not necessary in the case of this embodiment, as in other embodiments, to compress the nuts to a slightly oval shape in order to achieve the required tightness of the thread (the spindle must be selflocking); instead it is possible in this case to assemble the expansion appliance in the easy-running state and to then compress the member a little above the thicker threaded section in order to achieve the desired tightness.

Certain preferred embodiments of the invention are illustrated in the attached drawings in which:

FIG. 1 shows a longitudinal section through a first expansion appliance, taken along the longitudinal center plane B—B (FIG. 3);

FIG. 2 shows a front view of the expansion appliance;

FIG. 3 shows a side view of the expansion appliance;

FIG. 4 shows a cross-section through the expansion appliance, taken along line A—A in FIG. 1;

FIG. 5 shows a longitudinal section through a second expansion appliance, taken along the longitudinal center plane C—C (FIG. 7);

FIG. 6 shows a front view of the expansion appliance from FIG. 5;

FIG. 7 shows a side view of the expansion appliance from FIG. 5;

FIGS. 11 to 14 show views similar to FIGS. 1 to 4, but of a forth expansion appliance;

FIGS. 19 to 22 show views similar to FIGS. 1 to 4, but of a sixth expansion appliance.

Figure 8:
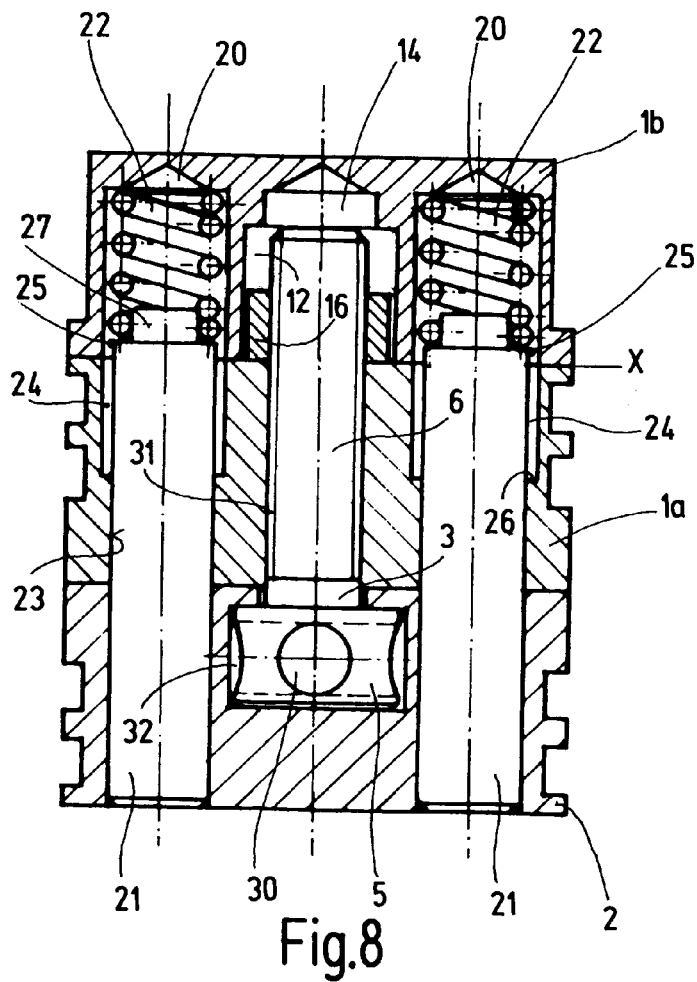
FIG. 8 shows a longitudinal section through a third expansion appliance, taken along the longitudinal center plane D—D (FIG. 10)

The expansion appliance illustrated in FIGS. 1 to 4 comprises two equal, approximately cuboid members 1 and 2 the relative spacing of which can be varied and which can be adjusted by a spindle 3. To this end, an orifice 4, intended to receive an actuating section 5 of the spindle, is provided in the two members 1 and 2, at their ends facing each other. The orifice 4 is provided half in the member 1 and half in the member 2.

The two members 1 and 2 are divided crosswise and consist of a first element 1a, 2a and a second element 1b, 2b. The partition planes X extend perpendicularly to the longitudinal direction of the spindle 3.

The spindle 3 is a double spindle; its actuating section 5 is followed by two threaded sections 6 and 7 that engage in orifices 8 and 9 in the two members 1 and 2. The orifices 8 and 9 have a shorter bore 10, 11, adjacent the orifice 4, which bore is closely fitted to a threadless shaft of the spindle 4 and which is followed by a non-cylindrical orifice 12, 13 extending to the end of the elements 1a, 2a, respectively, which in their turn are followed by cylindrical blind bores 14, 15 in elements 1b or 2b, respectively. The orifice 12, 13 is non-circular in order to accommodate a nut 16, 17, having a similarly non-circular lateral surface, in non-rotation fashion—see FIG. 4. The nuts 16, 17 are screwed onto threaded sections 6 and 7 of the spindle. A stop 18, 19 for the nuts 16, 17 is formed at each transition from the orifice 12, 13 to the bore 10, 11.

A cylindrical blind bore 20 is provided on both sides of the spindle 3 in each of the members 1 and 2. Two cylindrical guide rods 21 are supported in floating fashion in the blind bores 20, by means to two equal pseudoelastic coiled springs 22 arranged between the ends of the guide rods 21 and the closed ends of the blind bores 20. The coiled springs 22 serve as compression springs and are to this end pre-stressed to such an extent that they remain within the martensite plateau from the beginning until the end of their expansion range. Their expansion range is determined by the travel the nuts 16 and 17 can perform in the orifices 12, 13.

Starting from the ends of the two members 1 and 2, that face each other, the blind bores 20 exhibit initially a section 23 that serves as guide for the guide rods 21 and that is closely adapted to the outer diameter of the guide rods 21. This section is followed by a section 24 of somewhat larger diameter, which extends in part within the first element 1a, 2a of the members 1,2 and then into the second element 1b, 2b of the members 1, 2. This enlarged section 24 is utilized to provided, at the end of the guide rods 21, radial projections 15 that can be formed by upsetting, or alternatively by notching, and that limit the expansion range of the expansion appliance in that they abut against a shoulder 26 formed at the transition from the narrower guiding section 23 to the enlarged section 24 of the blind bores 20. In addition, the enlarged section 24 allows the coiled springs 22 to be given a somewhat larger outer diameter than the guide rods 21. Each of the guide rods 21 further carries on its end a thinner lengthwise extension 27 that engages a certain length in the adjacent coiled spring 22 so as to center it.

After installation of the spring 22, the guide rods 21 and the spindle 3 with the nuts 16 and 17, the first member elements 1a and 2a are welded to the second member elements 1b and 2a.

The members 1 and 2 are provided on their outside in the known fashion with retentions 28 that serve to anchor them positively in the casting resin of a palate plate, and further carry, until the time they are mounted in the palate plate as intended, a removable placeholder 29 that prevents any resin from flowing into the orifice 4 during casting of the palate plate.

At the beginning of the process of correcting the tooth position, the two members 1 and 2 are in contact one with the other, as shown in the drawing. The treatment begins by moving the nuts 16 and 17 apart by rotation of the spindle 3 so that they move away from the stops 18 and 19. The springs 22 now tend to urge the members 1 and 2 away one from the other, during which process the tooth position is gradually changed until the nuts 16 and 17 come to rest against the stop 18 and 19, respectively. By repeatedly actuating the spindle 3 in the described sense, the magnitude of correction of the tooth position can be increased, but this maximally until the radial projections 25 abut against the shoulders 28.

The spindle 3 can be operated by engaging a pin in one of four openings 30, arranged at an angular spacing of 90° in the actuating section 5, and by using the pin as a lever for rotating the spindle 3. The openings 30 are accessible in the orifice 4. The open access area 34, provided for rotating the spindle 3, can be seen in FIG. 2; this indicates the possible rotation of the spindle.

In the embodiment illustrated in FIGS. 5 to 7, similar parts or corresponding parts are designated by the same reference numerals as in the first embodiment. The expansion appliance according to FIGS. 5 to 7 comprises likewise two members 1 and 2 and two guide rods 21 and a spindle 3, but the latter has only one threaded section 6, which means that the spindle is a head spindle. The member 1, in which the threaded section 6 is engaged, is similarly structured as in the first embodiment and comprises again two elements 1a and 1b that must be welded together. But contrary to the first embodiment the threaded section 6 of the spindle is threaded into a threaded bore 31 provided directly in the first element 1a of the member 1. The point of the threaded section 6 extends—as in the first embodiment—into a cylindrical blind bore 14 in the second element 1b of the member 1.

Because of the threaded bore 31, the enlarged orifice with the loose nut provided in the first element 1a in the first embodiment does not exist in this embodiment.

To accommodate the head 5 of the spindle 3, an orifice 32 is provided in the second member 2, instead of the orifices in the two members 1 and 2. The orifice 32 is longer than the head 5 so that the latter can be displaced a certain length within the orifice 32. This corresponds to the longitudinal displacement of the nuts 16, 17 in the first embodiment, and determines the expansion range of the coiled springs 22.

The guide rods 21 are not floatingly supported, but are fastened in, for example pressed into and/or caulked in, through-bores in the second member 2. The guide rods 21 are thus permitted to slide only in the first member 1.

At the beginning of the process of correcting the tooth position the two members 1 and 2 are in contact one with the other, as illustrated in FIG. 5. By rotating the spindle 3, the latter is then screwed out a certain length from the member 1, whereby it moves away from the stop 33 that defines the end of the orifice 32 neighboring the member 1. The springs 22 now tend to urge the members 1 and 2 away one from the other, during which process the tooth position is gradually changed until the spindle head 5 comes to rest again against the stop 33. This process can be repeated until the expansion range of the expansion appliance is exhausted.

Since no springs are provided in the second member 2, but only the spindle head 5 is enclosed, and the guide rods 20 and 21 are fastened in the member 2, the latter may be shorter than the member 1. Consequently, the expansion appliance of FIGS. 5 and 7 may altogether be shorter than the expansion appliance according to FIGS. 1 to 4.

Figure 9:
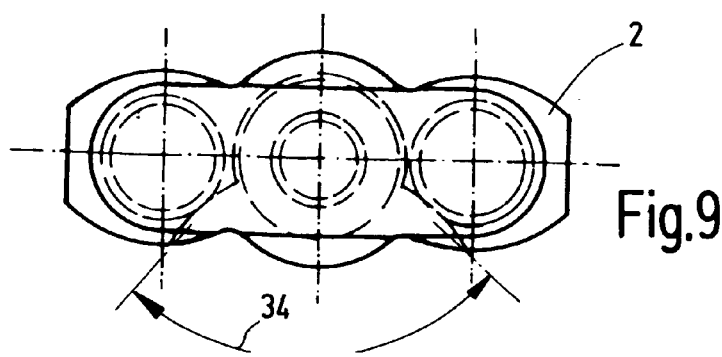
FIG. 9 shows a front view of the expansion appliance from FIG. 8.
Figure 10:
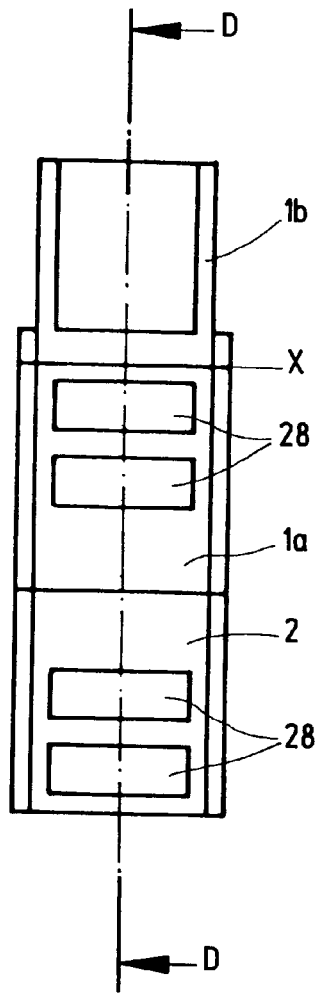
FIG. 10 shows a side view of the expansion appliance from FIG. 8.
Figure 16:
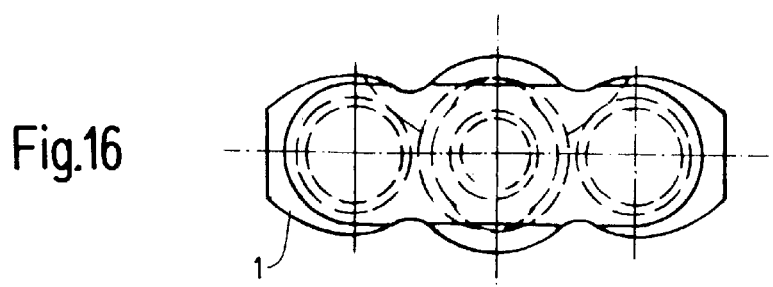
FIGS. 15 to 18 show views similar to FIGS. 1 to 4, but of a fifth expansion appliance.

The third embodiment of an expansion appliance illustrated in FIGS. 8 to 10 differs from the second embodiment illustrated in FIGS. 5 to 7 in that the spindle 3, with its head 5, is not arranged displaceably, but rather is fixed against displacement in an orifice 32 in the second member 2. In order to compensate for that, the threaded section 6 of the spindle is threaded not into a threaded bore of the first member 1, but into a nut 16 which is provided in a non-cylindrical orifice 12 in the first member 1 in non-rotatable but lengthwise displaceable fashion, similar to the arrangement of FIG. 1. By rotating the spindle 3, the nut 16 is advanced a certain length in the direction of the point of the threaded section 6 of the spindle, so that the springs 22 can expand by a similar length until the nut 16 comes again to abut on the stop 18 in the first member 1.

The forth embodiment illustrated in FIGS. 11 to 14 differs from the embodiment illustrated in FIGS. 1 to 4 in that the guide rods 21, instead of carrying a lengthwise extension 27, are provided on each of their ends with a blind bore 35 into which the coiled spring 22 engages over part of its length so that it is tensioned between the base of the blind bore 35 in the guide rod and the base of the blind bore 20 in the members 1 and 2. Contrary to the embodiment according to FIGS. 1 to 4, the blind bores 20 in the members 1 and 2 are not stepped, but have the same diameter over their full length. In combination with the longer guide rod this leads to an improved guiding effect for the members 1 and 2.

The fifth embodiment illustrated in FIGS. 15 to 18 differs from the forth embodiment illustrated in FIGS. 11 to 14 in that the coiled springs 22 are provided only on one end of the guide rods 21, namely in the member 2. In addition, the spindle 3 exhibits an asymmetrical design, with a thinner threaded section 7 that coacts with a nut 17, as in FIG. 4, and a thicker threaded section 36 which is threaded directly into a threaded bore of the single-piece member 1. The guide rods 21 are fixed in the member 1 and displaceable in the member 2. Given the fact that the threaded section 36 has a larger diameter than the threaded section 7, it was possible to give the threaded bore in the member 1 the form of a through-bore and to provide a diagonally extending slot 37 at the end of the threaded section 36, into which a screwdriver blade can be engaged for adjusting the spindle 3. This is easier than rotating the spindle by repeatedly turning it about a quarter circle, by engaging a pin in the radial bores 30 of the actuating section of the spindle.

Figures 15, 17:
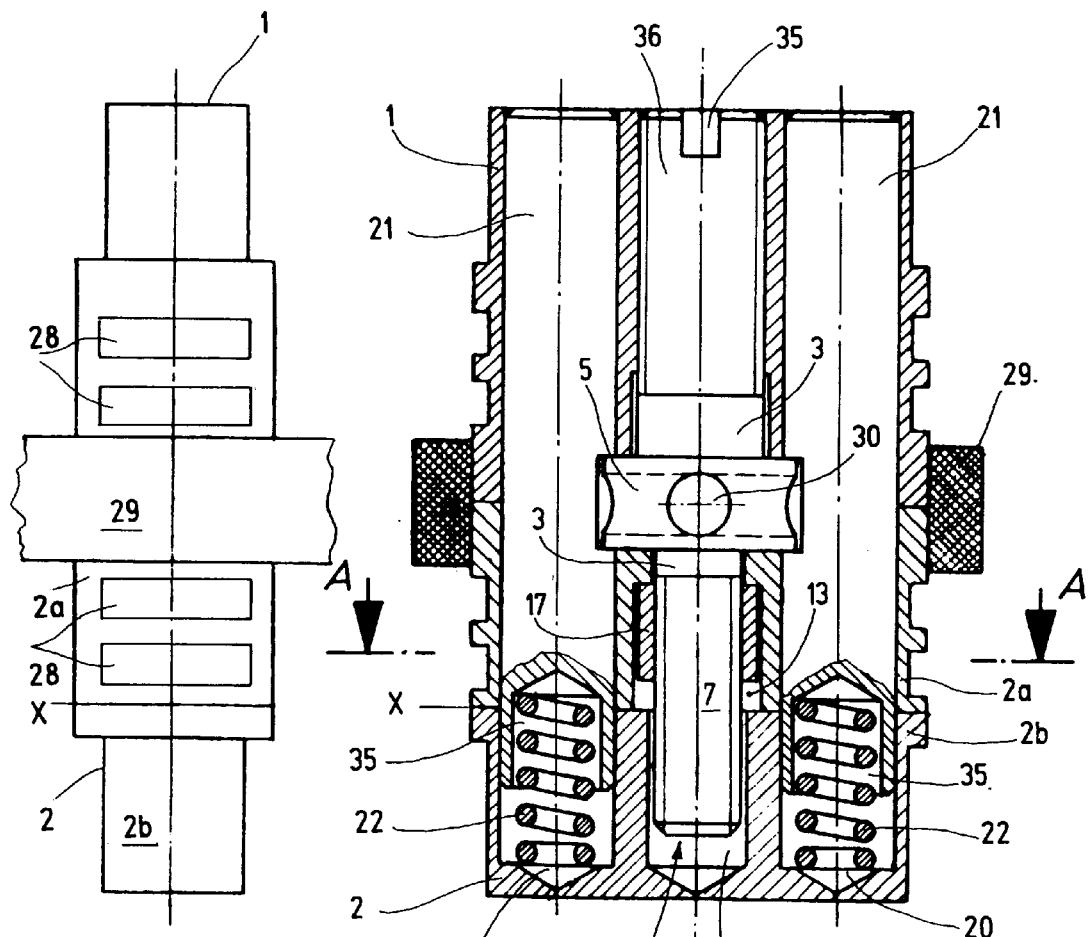
Figure 18:
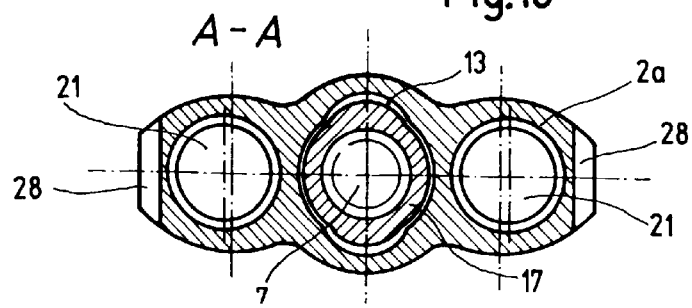

The sixth embodiment illustrated in FIGS. 19 to 22 differs from the fifth embodiment illustrated in FIGS. 15 and 18 in that the arrangement of the coiled springs 22 is the same as that selected in the examples of FIGS. 1 or 5 or 8.

Figure 23:
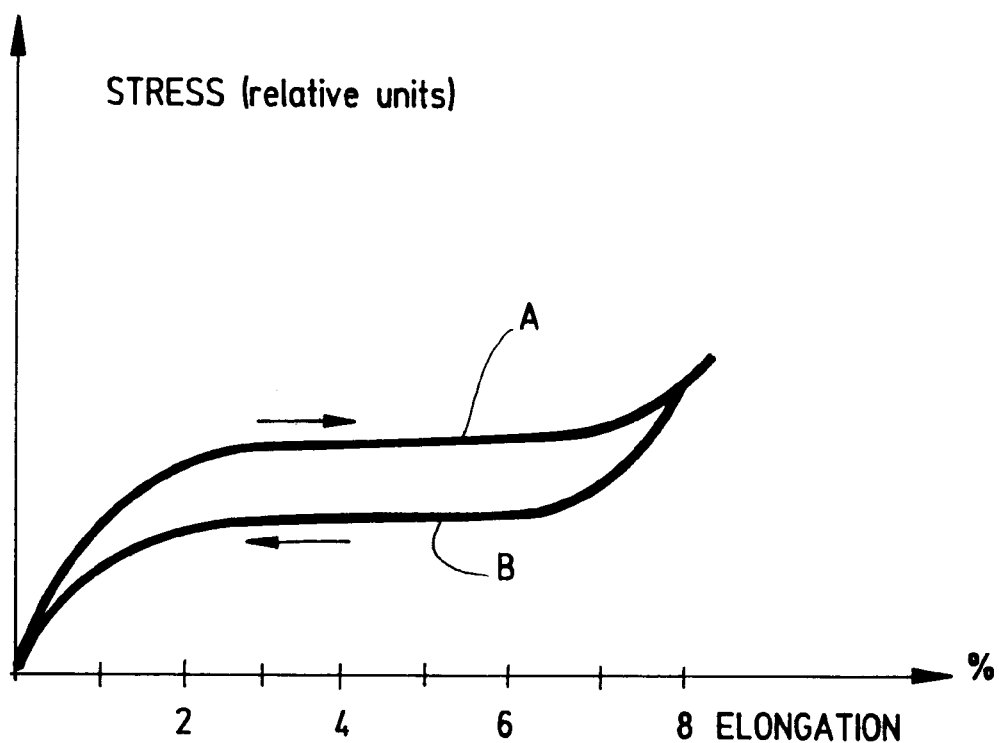
FIG. 23 shows a typical tensile stress/strain curve for a pseudoelastic wire.

FIG. 23 shows a typical tensile stress/strain curve for a pseudoelastic nickel/titanium wire. If such a wire is elongated by tension, a moderately rising tensile force is initially required for progressively elongating the wire. After an elongation of approximately 3%, the tensile force required to achieve further progressive elongation then rises only slightly until it starts again to rise more steeply at an elongation of approximately 8% (upper branch A of the curve).

When the tension on the wire is then released, the elongation reverts along the lower branch B of the curve. This demonstrates the presence of hysteresis. The flat section of the curve, in the illustrated example between 2% and 8%, being known as martensite plateau, is utilized for purposes of the invention. The rising section of the curve, between 0 and approximately 2% elongation, which is less effective for connection of the tooth position, can be eliminated for purposes of correcting the tooth position by installing the springs 22 with a corresponding prestress.

What is claimed is:

1. Expansion appliance for correcting tooth misalignments having the following features:
    a first member (1);
    a second member (2);
    a spindle (3) which, for changing the relative distance between the first (1) and the second member (2), engages in the two members (1,2) in such a way that the distance can be varied by a predeterminable limited magnitude in the longitudinal direction of the spindle (3) while the spindle (3) is in a stationary position,
    there are provided two parallel guide rods (21), located on both sides of the spindle (3);
    for guiding the first member (1) and the second member (2) in straight alignment the guide rods (21) are received and guided in holes (20) in the two members (1,2), which extend in parallel one to the other and each of which is open toward the respective other member (2, 1);
    a compression spring (22) is disposed and tensioned between at least one end of each guide rod (21) and the respective opposite end of the hole (20), this end of the hole (20) being closed, wherein the compression spring is disposed together with the respective guide rod (21) in the same hole (20).

2. The expansion appliance as defined in claim 1, in which
    the spindle (3) comprises an actuating section (5) and, projecting therefrom, two threaded sections (6, 7) which extend in opposite directions and whose threads are oppositely directed;
    the threaded sections (6, 7) extend into orifices (8, 9) provided in the two members (1, 2);
    at least one of the two orifices (8, 9) accommodates a nut (16, 17) that is screwed onto the threaded section (6, 7) located in the respective orifice (8, 9);
    the nut (16, 17) is secured against rotation in the at least one orifice (8, 9) and can be displaced along the threaded section (6, 7) of the spindle (3) by rotation of the spindle (3);
    a stop (18, 19) for the nut (16, 17) is provided in the at least one orifice (8, 9) between the actuating section (5) of the spindle (3) and the nut (16, 17).

3. The expansion appliance as defined in claim 2, in which a nut (16, 17) is provided in both orifices (8, 9) and a stop (18, 19) for the nut (16, 17) is provided in both orifices (8, 9) between the actuating section (5) of the spindle (3) and the respective nut (16, 17).

4. The expansion appliance as defined in claim 2, characterized in that a nut (17) is arranged only in one orifice (13) and that the other orifice is configured as a threaded bore (31) in the respective member (1).

5. The expansion appliance as defined in claim 1, in which
    the spindle (3) comprises an actuating section (5) and, projecting therefrom, two threaded sections (6, 7);
    the actuating section (5) of the spindle (3) is arranged in an orifice (32) in the second member (2);
    the threaded section (6) extends into an orifice (8) provided in the first member (1);
    a nut (16) is provided in the orifice (8), the nut being screwed onto the threaded section (6) located in the orifice (8);
    the nut (16) is secured against rotation in the orifice (8) and can be displaced along the threaded section (6) of the spindle (3) by rotation of the spindle (3);
    a stop (18) for the nut (16) is provided in the orifice (8) between the actuating section (5) of the spindle (3) and the nut (16);
    a stop (33) for the actuating section (5) is provided in the orifice (32 between the actuating section (5) of the spindle (3) and the first member (1),
    the actuating section (5) can be displaced in the orifice (32) not at all or only by a limited amount.

6. The expansion appliance as defined in claim 5, characterized in that the guide rods (21) are fixed in the second member (2) and that the springs (22) are arranged only in the first member (1).

7. The expansion appliance as defined in claim 1, 2, 3, or 5, characterized in that the guide rods (21) and the sections (23) of the holes (20) guiding them are cylindrical in shape.

8. The expansion appliance as defined in claim 1, characterized in that the holes (20) comprise, between a section

(23) guiding the guide rods (21) and their ends, a section (24) whose interior width is larger than that of the section (23) that guides the guide rod (21).

9. The expansion appliance as defined in claim 8, characterized in that the guide rods (21) carry on those of their ends, on which a spring (22) is arranged, a radial projection (25) that prevents the guide rod (21) from sliding through the section (23) of the hole (20) that serves as a guide.

10. The expansion appliance as defined in claim 8, characterized in that the members (1,2) are divided crosswise into elements (1a,1b; 2a,2b) and that the two elements (1a,1b; 2a,2b) of a respective one of the members (1,2) are firmly joined one to the other, the partition face (X) intersecting the enlarged sections (24) of the holes (20).

11. The expansion appliance as defined in claim 10, characterized in that the elements (1a,1b; 2a,2b) of the first member (1) and of the second member (2) are joined by welding or hard soldering.

12. The expansion appliance as defined in claim 1, characterized in that a spring (22) is arranged on both ends of each guide rod (21).

13. The expansion appliance as defined in claim 12, characterized in that the springs (22) are equal one to the other.

14. The expansion appliance as defined in claim 1, characterized in that the springs (22) are pseudoelastic.

15. The expansion appliance as defined in claim 1, characterized in that the spindle (3) comprises an actuating section (5) and, projecting therefrom, two threaded sections (6,7);

the actuating section (6) of the spindle (3) is arranged in an orifice (32) in the second member (2);

the threaded section (6) extends into an orifice (8) provided in the first member (1);

the springs (22) are coiled springs whose outer diameters are larger than that of the guide rods (21).

16. The expansion appliance as defined in claim 1, characterized in that the guide rods (21) are provided on their ends, on which the coiled springs (22) are arranged, with a thin lengthwise extension (27) that engages a certain length in the adjacent coiled spring (22).

17. The expansion appliance as defined in claim 1, characterized in that the guide rods (21) are provided on their ends, in which the coiled springs (22) are arranged, with a longitudinally extending blind bore (20) in which the adjacent coiled spring (22) engages over part of its length.

18. The expansion appliance as defined in claim 1, characterized in that the springs (22) are made of shape-memory alloys based on nickel and titanium and containing nickel and titanium in about equal atomic percentages.

19. The expansion appliance as defined in claim 1, characterized in that the springs (22) are made of an alloy showing substantially that the force required for increasing elongation of the material initially rises sharply as in the case of an austenite, but then after reaching an elongation of approximately 1 percent to 2 percent, increases only slightly, and does not increase steeply again until reaching greater elongations of 6 percent to 8 percent.

20. Expansion appliance for correcting tooth misalignments having the following features:

a first member (1);

a second member (2);

a spindle (3) which, for changing the relative distance between the first (1) and the second member (2), engages in the two members (1,2) in such a way that the distance can be varied by a predeterminable limited magnitude in the longitudinal direction of the spindle (3) while the spindle (3) is in a stationary position, there are provided two parallel guide rods (21), located on both sides of the spindle (3);

for guiding the first member (1) and the second member (2) in straight alignment the guide rods (21) are received and guided in holes (20) in the two members (1,2), which extend in parallel one to the other and each of which is open toward the respective other member (2, 1);

a compression spring (22) is tensioned between at least one end of each guide rod (21) and the respective opposite end of the hole (20), this end of the hole (20) being closed;

wherein the spindle (3) comprises an actuating section (5) and, projecting therefrom, a threaded section (6);

the actuating section (5) of the spindle (3) is arranged in an orifice (32) in the second member (2);

the threaded section (6) sits in a threaded bore (31) provided in the first member (1);

the actuating section (5) of the spindle (3) can be displaced in that orifice (32) by rotation of the spindle (3);

a stop (33) for the actuating section (5) is provided in the orifice (32) between the actuating section (5) of the spindle (3) and the first member (1).

21. The expansion appliance as defined in claim 20, characterized in that the guide rods (21) and the sections (23) of the holes (20) guiding them are cylindrical in shape.

22. The expansion appliance as defined in claim 20, characterized in that the guide rods (21) are fixed in the second member (2) and that the springs (22) are arranged only in the first member (1).

23. Expansion appliance for correcting tooth misalignments having the following features:

a first member (1);

a second member (2);

a spindle (3) for varying the relative spacing between the first (1) and the second member (2);

the spindle (3) comprises an actuating section (5) and projecting therefrom, two threaded sections (6,7), which extend in opposite directions and have oppositely directed threads;

the threaded sections (6,7) extend into orifices (8,9) provided in the two members (1,2);

each of the two orifices (8,9) accommodates a nut (16,17) that is screwed onto threaded section (6,7) located in the respective orifice (8,9);

the nut (16,17) is secured against rotation in the orifice (8,9) and displaceable along the threaded section (6,7) of the spindle (3) by rotation of the spindle (3);

a stop (18,19) for the nut (16,17) is provided in the orifices (8,9) between the actuating section (5) of the spindle (3) and the respective nut (16,17);

there are provided two parallel guide rods (21), located on both sides of the spindle (3);

for guiding the first member (1) and the second member (2) in straight alignment the guide rods (21) are received and guided in holes (20) in the two members (1,2), which extend in parallel one to the other and each of which is open toward the respective other member (2, 1);

a pseudoelastic compression spring (22) is tensioned between at least one end of each guide rod (21) and the respective opposite end of the hole (20), this end of the hole (20) being closed.

24. Expansion appliance for correcting tooth misalignments having the following features:

a first member (1);

a second member (2);

a spindle (3) for varying the relative spacing between the first (1) and the second member (2);

the spindle (3) comprises an actuating section (5) and, projecting therefrom, a threaded section (6);

the actuating section (5) of the spindle (3) is arranged in an orifice (32) of the second member (2);

there are provided two parallel guide rods (21), located on both sides of the spindle (3);

for guiding the members (1, 2) in straight alignment the guide rods (21) are received and guided in holes (20) in the two members (1, 2), which extend in parallel one to the other and each of which is open toward the respective other member (2, 1);

the threaded section (6) sits in a threaded bore (31) provided in the first member (1), the actuating section (5) of the spindle (3) can be displaced in the orifice (32) by rotation of the spindle (3);

a stop (33) for the actuating section (5) is provided in the orifice (32) between the actuating section (5) of the spindle (3) and the first member (1);

a compression spring (22) is tensioned between at least one end of each guide rod (21) and the respective opposite end of the hole (22), this end of the hole (20) being closed.

25. Expansion appliance for correcting tooth misalignments having the following features:

a first member (1);

a second member (2);

a spindle (3) for varying the spacing between the first (1) and the second member (2);

the spindle (3) comprises an actuating section (5) and, projecting therefrom, a threaded section (6);

the actuating section (5) of the spindle (3) is arranged in an orifice (32) in the second member (2);

the threaded section (6) extends into an orifice (8) provided in the first member (1);

a nut (16) is provided in the orifice (8), the nut being screwed onto the threaded section (6) located in the orifice (8);

the nut (16) is secured against rotation in the orifice (8) and can be displaced along the threaded section (6) of the spindle (3) by rotation of the spindle (3);

a stop (18) for the nut (16) is provided in the orifice (8) between the actuating section (5) of the spindle (3) and the nut (16).

* * * * *